(12) United States Patent
Bittar et al.

(10) Patent No.: US 8,854,044 B2
(45) Date of Patent: Oct. 7, 2014

(54) INSTRUMENTED CORE BARRELS AND METHODS OF MONITORING A CORE WHILE THE CORE IS BEING CUT (71) Applicant: Halliburton Energy Services, Inc., Houston, TX (US)

(72) Inventors: Michael S. Bittar, Houston, TX (US); Gary E. Weaver, Conroe, TX (US)

(73) Assignee: Haliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/659,250

(22) Filed: Oct. 24, 2012

(65) Prior Publication Data
US 2013/0113487 A1 May 9, 2013

(30) Foreign Application Priority Data
Nov. 9, 2011 (WO) ................ PCT/US2011/059947

(51) Int. Cl.
G01V 3/00 (2006.01)
G01N 27/02 (2006.01)
G01N 33/24 (2006.01)
G01V 3/28 (2006.01)

(52) U.S. Cl.
CPC ................ *G01V 3/28* (2013.01); *G01N 27/025* (2013.01); *G01N 33/24* (2013.01)
USPC ............ 324/333; 324/338; 324/376; 324/377

(58) Field of Classification Search
CPC ....... G01N 33/24; G01N 27/025; G01V 3/28; G01V 3/30; G01V 3/18; G01V 3/12; E21B 47/122

USPC ................ 324/333, 338, 339, 342, 343, 323, 324/344–377; 175/46, 58; 73/152.09, 73/152.11, 152.07
See application file for complete search history.

(56) References Cited

U.S. PATENT DOCUMENTS 2,921,253 A * 1/1960 Liben ............................ 324/355
3,479,001 A 11/1969 Dower
(Continued)

FOREIGN PATENT DOCUMENTS

CN 101037941 A 9/2007
WO 2009062716 A2 5/2009
(Continued)

OTHER PUBLICATIONS

International Search Report with Written Opinion issued Nov. 30, 2009 for International Patent Application No. PCT/US09/059534, 8 pages.

(Continued)

Primary Examiner — Tung X Nguyen
Assistant Examiner — Raul Rios Russo
(74) Attorney, Agent, or Firm — Smith IP Services, P.C.

(57) ABSTRACT

A formation core analysis system can include an inner barrel and a toroidal electromagnetic antenna which transmits electromagnetic signals into a formation core when the core is received in the inner barrel. Another formation core analysis system can include an inner barrel and multiple longitudinally spaced apart electrodes which electrically contact a formation core when the core is received in the inner barrel. A speed of displacement of the core into the inner barrel may be indicated by differences between measurements taken via the electrodes as the core displaces into the inner barrel. A method of measuring resistivity of a formation core as the core is being cut can include transmitting electromagnetic signals into the core from a toroidal electromagnetic antenna as the core is being cut by a coring bit.

31 Claims, 4 Drawing Sheets (56) References Cited

U.S. PATENT DOCUMENTS

| | | | |
|---|---|---|---|
| 3,605,920 | A | 9/1971 | Woodward |
| 4,393,350 | A | 7/1983 | Hansen et al. |
| 4,492,275 | A | 1/1985 | Campbell et al. |
| 4,499,955 | A | 2/1985 | Campbell et al. |
| 4,578,675 | A | 3/1986 | MacLeod |
| 4,596,143 | A | 6/1986 | Norel |
| 4,601,354 | A | 7/1986 | Campbell et al. |
| 4,735,269 | A * | 4/1988 | Park et al. .............. 175/46 |
| 4,940,943 | A | 7/1990 | Bartel et al. |
| 5,050,690 | A | 9/1991 | Smith |
| 5,095,273 | A * | 3/1992 | Kennedy et al. .............. 324/376 |
| 5,160,925 | A | 11/1992 | Dailey et al. |
| 5,235,285 | A | 8/1993 | Clark et al. |
| 5,339,036 | A | 8/1994 | Clark et al. |
| 5,501,285 | A | 3/1996 | Lamine et al. |
| 5,508,616 | A | 4/1996 | Sato et al. |
| 5,568,838 | A | 10/1996 | Struthers et al. |
| 5,726,951 | A | 3/1998 | Birchak et al. |
| 5,984,023 | A | 11/1999 | Sharma et al. |
| 6,006,844 | A * | 12/1999 | Van Puymbroeck et al. ... 175/50 |
| 6,176,323 | B1 | 1/2001 | Weirich et al. |
| 6,181,138 | B1 | 1/2001 | Hagiwara et al. |
| 6,220,371 | B1 | 4/2001 | Sharma et al. |
| 6,304,086 | B1 | 10/2001 | Minerbo et al. |
| 6,374,925 | B1 | 4/2002 | Elkins et al. |
| 6,457,538 | B1 * | 10/2002 | Pittard et al. .............. 175/46 |
| 6,480,118 | B1 | 11/2002 | Rao |
| 6,710,601 | B2 * | 3/2004 | Rosthal et al. .............. 324/343 |
| 6,778,127 | B2 | 8/2004 | Stolarczyk et al. |
| 6,788,066 | B2 * | 9/2004 | Wisler et al. .............. 324/376 |
| 6,791,469 | B1 | 9/2004 | Rao et al. |
| 6,819,110 | B2 | 11/2004 | Omeragic et al. |
| 6,944,547 | B2 | 9/2005 | Womer et al. |
| 6,958,610 | B2 | 10/2005 | Gianzero |
| 7,046,165 | B2 | 5/2006 | Beique et al. |
| 7,138,897 | B2 | 11/2006 | Minerbo et al. |
| 7,168,508 | B2 | 1/2007 | Goldberg et al. |
| 7,185,719 | B2 | 3/2007 | Van Riet |
| 7,265,649 | B1 | 9/2007 | Hall et al. |
| 7,293,613 | B2 | 11/2007 | Goldberg et al. |
| 7,350,568 | B2 | 4/2008 | Mandal et al. |
| 7,414,406 | B2 | 8/2008 | Banning et al. |
| 7,436,184 | B2 * | 10/2008 | Moore .............. 324/347 |
| 7,500,388 | B2 | 3/2009 | Fujisawa et al. |
| 7,612,565 | B2 | 11/2009 | Seydoux et al. |
| 7,659,722 | B2 | 2/2010 | Bittar |
| 7,665,542 | B2 | 2/2010 | Stockton |
| 7,748,265 | B2 | 7/2010 | Reid et al. |
| 8,072,221 | B2 | 12/2011 | Snyder, Jr. et al. |
| 2001/0046811 | A1 * | 11/2001 | Fleury et al. .............. 439/610 |
| 2001/0050559 | A1 * | 12/2001 | Wisler et al. .............. 324/377 |
| 2002/0169559 | A1 | 11/2002 | Onyia et al. |
| 2003/0168257 | A1 | 9/2003 | Aldred et al. |
| 2004/0183538 | A1 | 9/2004 | Hanstein et al. |
| 2005/0252286 | A1 | 11/2005 | Ibrahim et al. |
| 2006/0017443 | A1 | 1/2006 | Folberth et al. |
| 2006/0244455 | A1 | 11/2006 | Bittar |
| 2007/0168056 | A1 | 7/2007 | Shayegi et al. |
| 2007/0256832 | A1 | 11/2007 | Hagiwara et al. |
| 2007/0285274 | A1 | 12/2007 | Esmersoy |
| 2008/0078580 | A1 | 4/2008 | Bittar |
| 2008/0258733 | A1 | 10/2008 | Bittar |
| 2008/0297161 | A1 | 12/2008 | Gorek |
| 2009/0105955 | A1 * | 4/2009 | Castillo et al. .............. 702/7 |
| 2009/0139768 | A1 | 6/2009 | Castillo |
| 2009/0150076 | A1 | 6/2009 | Taherian et al. |
| 2009/0159335 | A1 * | 6/2009 | Cravatte .............. 175/40 |
| 2009/0166088 | A1 | 7/2009 | Jeffryes et al. |
| 2009/0224764 | A1 * | 9/2009 | Bittar .............. 324/338 |
| 2009/0230968 | A1 | 9/2009 | Bittar et al. |
| 2010/0000792 | A1 * | 1/2010 | Alberty .............. 175/50 |
| 2010/0179762 | A1 | 7/2010 | Tabarovsky et al. |
| 2011/0083905 | A1 * | 4/2011 | Cravatte .............. 175/239 |
| 2011/0180327 | A1 | 7/2011 | Bittar et al. |
| 2011/0290562 | A1 | 12/2011 | Standifird |
| 2011/0298461 | A1 | 12/2011 | Bittar |
| 2012/0081121 | A1 * | 4/2012 | Maurer et al. .............. 324/333 |
| 2012/0186873 | A1 | 7/2012 | Shayegi et al. |
| 2013/0113488 | A1 | 5/2013 | Bittar et al. |

FOREIGN PATENT DOCUMENTS

| | | |
|---|---|---|
| WO | 2010005902 A2 | 1/2010 |
| WO | 2010050840 A1 | 5/2010 |
| WO | 2011043851 A1 | 4/2011 |
| WO | 2011044069 A1 | 4/2011 |
| WO | 2011090480 A1 | 7/2011 |

OTHER PUBLICATIONS

International Search Report with Written Opinion issued Nov. 25, 2009 for International Patent Application No. PCT/US09/059541, 8 pages.

International Search Report with Written Opinion issued Nov. 25, 2009 for International Patent Application No. PCT/US09/059545, 8 pages.

International Search Report with Written Opinion issued Feb. 1, 2011 for International Patent Application No. PCT/US10/036851, 9 pages.

Rigzone; "Featured Employer: At Balance", online article, dated 1999-2011, 2 pages.

Schlumberger; "Managed Pressure Drilling & Underbalanced Drilling", online article, dated 2011, 2 pages.

Schlumberger, Don Reitsma; "Technical Paper: An Automated System for Accurate and Rapid Detection of Drilling Anomalies", technical paper, No. 140255, IADC Society, dated 2011, 2 pages.

ERC Equipoise; "ERC Equipoise Limited", company information, retrieval date Sep. 9, 2011, 9 pages.

Halliburton; "The Key to Drilling Optimization and Managed Pressure Drilling", Informational article, dated Oct. 2007, 8 pages.

Halliburton; "GeoBalance Optimized Pressure Drilling Services", H06382, dated Jan. 2009, 12 pages.

Search Report issued Aug. 30, 2012 for International Application Serial No. PCT/US11/59947, 5 pages.

Written Opinion issued Aug. 30, 2012 for International Application Serial No. PCT/US11/59947, 4 pages.

Office Action issued Jan. 15, 2014 for U.S. Appl. No. 13/659,273, 38 pages.

Office Action issued Jan. 16, 2014 for U.S. Appl. No. 13/201,031, 20 pages.

Halliburton; "New InSite Generation Resistivity Sensor Combines Geosteering/Formation Evaluation While Drillinf to Optimize Wellbore Placement in Complex, Deviated and Horizontal Wells", Fuel from Knowledge Central article, dated Jul. 2007, 10 pages.

PBORE; "History", company brochure, dated Mar. 13, 1996, 6 pages.

SPE International; "Real-Time Basin Modeling: Improving GeoPressure and Earth-Stress Predictions", SPE 96464, dated Sep. 6-9, 2005, 6 pages.

SPE International; "New Data Transmission Standard Facilities Synchronous Remote Modeling and Surveillance via the Internet" SPE 99466, dated Apr. 11-13, 2006, 9 pages.

SPE International & IADC; "Novel Approach for Estimating Pore Fluid Pressures Ahead of the Drill Bit", SPE/IADC 104606, dated Feb. 20-22, 2007, 13 pages.

Halliburton; "StressCheck Software", Landmark article H04872, dated Aug. 2006, 4 pages.

Halliburton; "StressCheck Software", Landmark article H04972, dated Aug. 2006, 4 pages.

International Search Report with Written Opinion issued Aug. 30, 2012 for International Patent Application No. PCT/US11/059947, 9 pages.

International Search Report with Written Opinion issued Aug. 30, 2012 for International Patent Application No. PCT/US11/059950, 10 pages.

Office Action issued Apr. 17, 2014 for U.S. Appl. No. 13/659,273, 44 pages.

International Search Report with Written Opinion issued Dec. 3, 2010 for PCT Patent Application No. PCT/US10/051384, 8 pages.

(56) References Cited

OTHER PUBLICATIONS

V.A. Akinbinu; "Prediction of Fracture Gradient from Formation Pressures and Depth Using Correlation and Stepwise Multiple Regression Techniques", Journal of Petroleum Science and Engineering, vol. 72, pp. 10-17, dated Feb. 16, 2010, 8 pages.

W.A. Zoeller; "Pore Pressure Detection From the MWD Gamma Ray", SPE 12166, dated Oct. 5-8, 1983, 12 pages.

Specification and Drawings for PCT Patent Application No. PCT/US09/59541, Filed Oct. 5, 2009, Titled "Well Drilling Method Utilizing Real Time Response to Ahead of Bit Measurements", 25 pages.

Notice of Allowance issued Jun. 6, 2014 for U.S. Appl. No. 13/659,273, 10 pages.

Office Action issued May 15, 2014 for U.S. Appl. No. 13/144,321, 23 pages.

* cited by examiner

INSTRUMENTED CORE BARRELS AND METHODS OF MONITORING A CORE WHILE THE CORE IS BEING CUT

CROSS-REFERENCE TO RELATED APPLICATION

This application claims the benefit under 35 USC §119 of the filing date of International Application Serial No. PCT/US11/59947, filed 9 Nov. 2011. The entire disclosure of this prior application is incorporated herein by this reference.

BACKGROUND

This disclosure relates generally to equipment utilized and operations performed in conjunction with a subterranean well and, in one example described below, more particularly provides an instrumented core barrel and a method of monitoring a core while it is being cut.

The sampling of earth formations by coring operations can provide valuable insights into the characteristics of those formations. However, it is sometimes difficult to determine whether or how fast a core is being cut, whether the core is displacing properly into a core barrel assembly, the exact depth at which the core was cut, etc. It will, therefore, be readily appreciated that improvements are continually needed in the art of monitoring core cutting operations.

DETAILED DESCRIPTION

Figure 1:
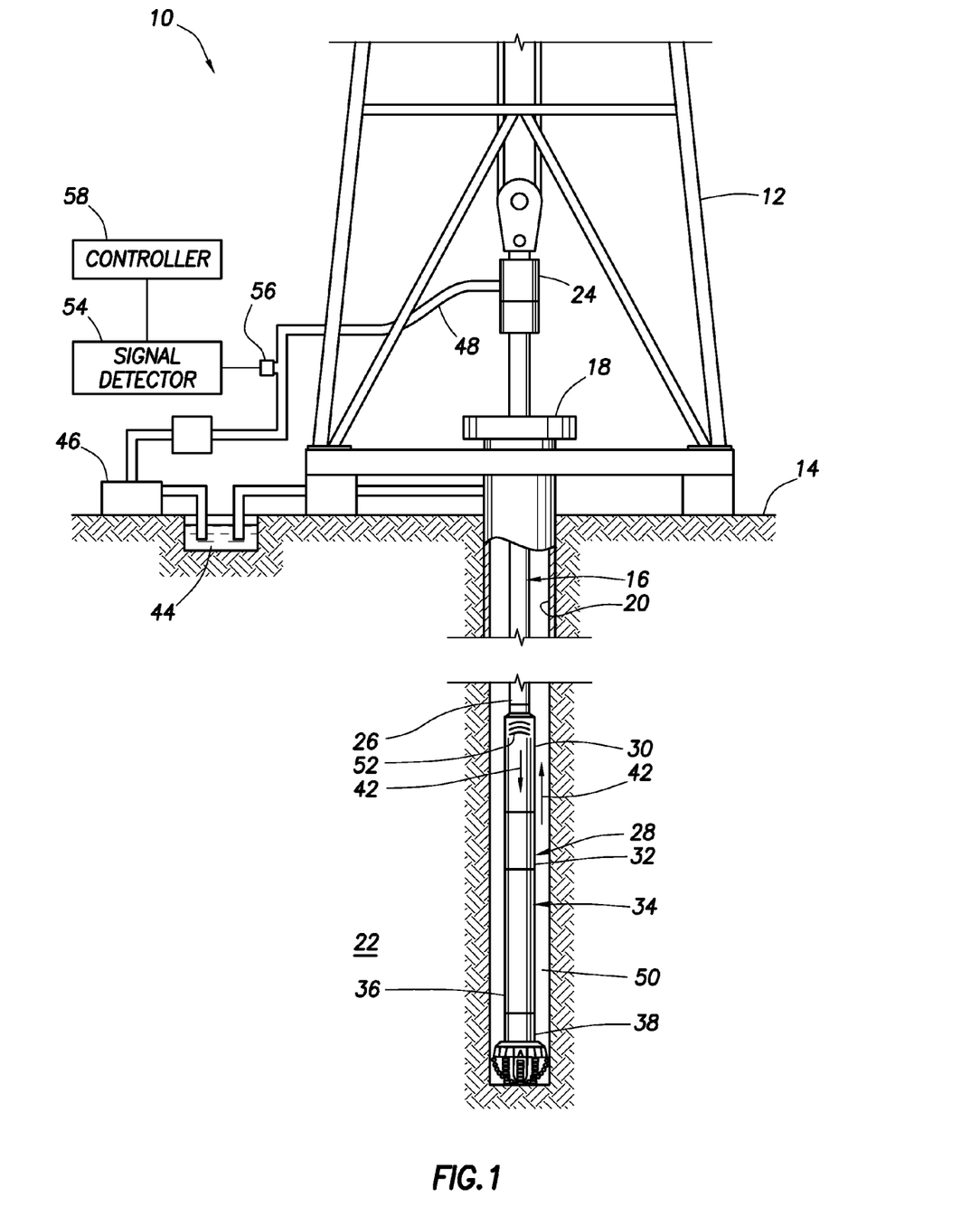
FIG. 1 is a representative cross-sectional view of a well system and associated method which can embody principles of this disclosure.

Representatively illustrated in FIG. 1 is an example of a well system 10 and associated method which can embody principles of this disclosure. However, it should be understood that the scope of this disclosure is not limited at all to the details of the well system 10 and method described herein and/or depicted in the drawings, since a wide variety of different well systems and methods can incorporate the principles of this disclosure.

In the FIG. 1 example, a drilling derrick 12 is located at or near the earth's surface 14, for supporting a drill string 16. The drill string 16 extends through a rotary table 18 and into a borehole 20 that is being drilled through an earth formation 22. In other examples, the derrick 12 may not be used, the surface 14 could be a sea floor or mudline, etc.

The drill string 16 may include a kelly 24 at its upper end, with drill pipe 26 coupled to the kelly 24. In other examples, a top drive or coiled tubing drilling rig could be used. Thus, it will be appreciated that the scope of this disclosure is not limited to any particular type of drilling equipment, or to any particular location of the drilling equipment.

A bottom hole assembly 28 (BHA) is coupled to a distal end of the drill pipe 26. The BHA 28 may include drill collars 30, a telemetry module 32 and a formation core analysis system 34. The core analysis system 34 can include a core barrel assembly 36 and a coring bit 38.

In operation, the kelly 24, the drill pipe 26 and the BHA 28 may be rotated by the rotary table 18. In other examples, a downhole motor (such as a positive displacement motor or a turbine) may be used to rotate the bit 38.

Weight applied through the drill collars 30 to the coring bit 38 causes the bit to drill through the formation 22 while generating a formation core 40 (see FIG. 2) that enters into the core barrel assembly 36. The core 40 is stored in the core barrel assembly 36, and may be retrieved from the borehole 20 for inspection at the surface 14.

During this coring operation, drilling fluid 42 (commonly referred to as "drilling mud") may be pumped from a mud pit 44 at the surface 14 by a pump 46, so that the drilling fluid flows through a standpipe 48, the kelly 24, through drill string 16, and to the coring bit 38. The drilling fluid 42 is discharged from the coring bit 38 and functions to cool and lubricate coring bit, and to carry away earth cuttings made by the bit.

After flowing through the coring bit 38, the drilling fluid 42 flows back to the surface 14 through an annulus 50 between the drill string 16 and the borehole 20. The drilling fluid 42 is returned to the mud pit 44 for filtering and conditioning.

In this example, the circulating column of drilling fluid 42 flowing through the drill string 16 may also function as a medium for transmitting pressure signals 52 carrying information from telemetry module tool 32 to the surface 14. A pressure signal 52 travelling in the column of drilling fluid 42 may be detected at the surface 14 by a signal detector 54 employing a suitable pressure sensor 56.

The pressure signals 52 may be encoded binary representations of measurement data indicative of downhole coring parameters discussed more fully below. The detected signals 52 may be decoded by a surface controller 58.

The surface controller 58 may be located proximate to or remote from the derrick 12. In one example, the controller 58 may be incorporated as part of a logging unit.

In other examples, the controller 58 (and/or any other elements of the core analysis system 34) may be positioned at a subsea location, in the wellbore 20, as part of the BHA 28, or at any other location. The scope of this disclosure is not limited to any particular location of elements of the system 34.

Alternatively, other telemetry techniques, such as electromagnetic and/or acoustic techniques, or any other suitable technique, may be utilized. In one example, hard wired drill pipe (e.g., the drill pipe 26 having lines extending in a wall thereof) may be used to communicate between the surface 14 and the BHA 28. In other examples, combinations of various communication techniques may be used (e.g., short hop acoustic or electromagnetic telemetry with long hop electrical or optical communication, etc.).

Figure 2:
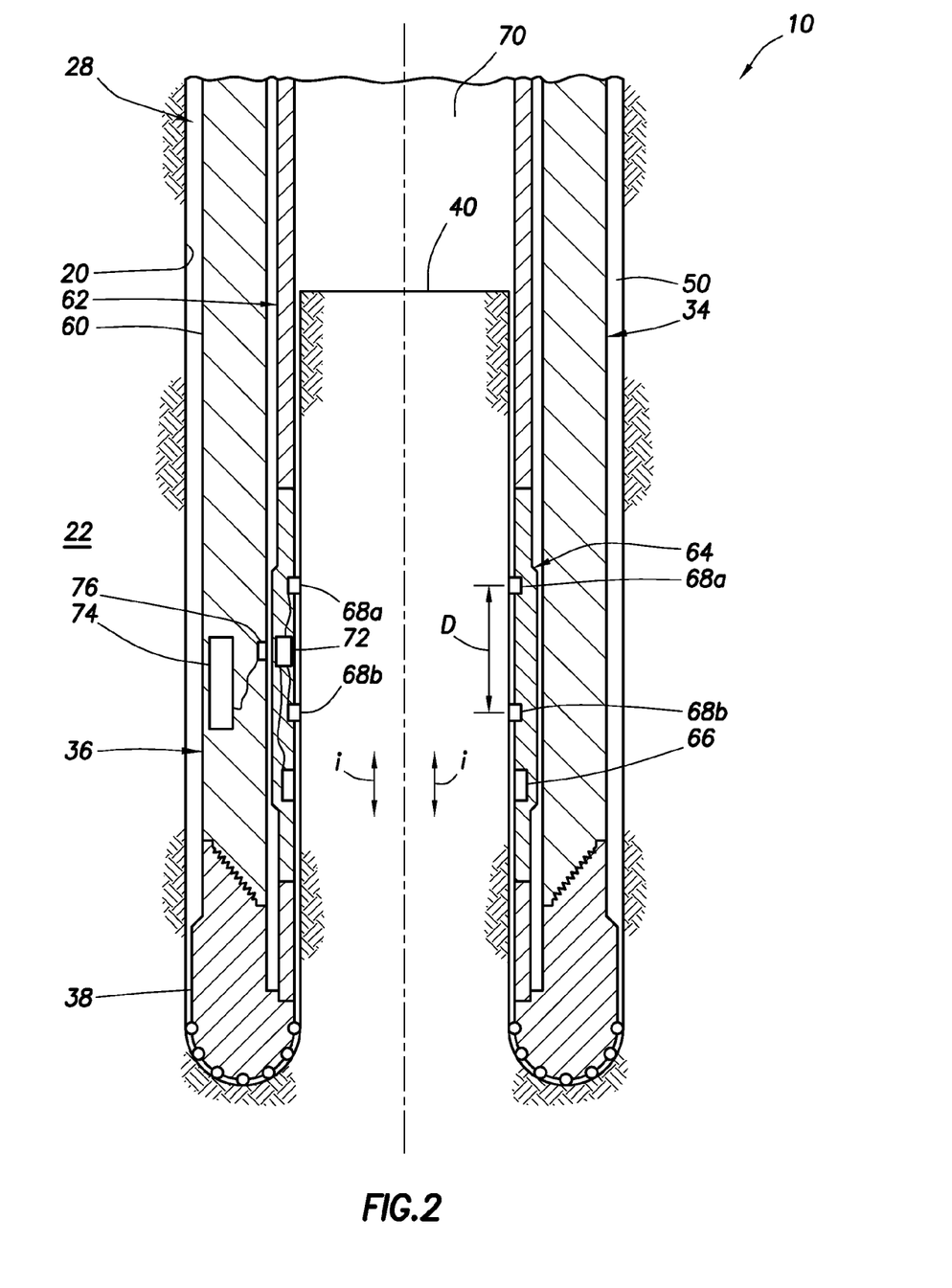
FIG. 2 is a representative cross-sectional view of a formation core analysis system which can embody principles of this disclosure, and which may be used in the well system of FIG. 1.

Referring additionally now to FIG. 2, a more detailed example of the core analysis system 34 is representatively illustrated. In this example, the core barrel assembly 36 includes an outer barrel 60 and an inner barrel 62 mounted substantially concentrically inside the outer barrel.

The coring bit 38 is attached to the distal end of the outer barrel 60. Bearings and seals (not shown) can be provided to allow the outer barrel 60 to rotate relative to the formation 22 during the coring operation, while the inner barrel 62 remains substantially non-rotating with respect to the formation. Such bearing and seal arrangements are known in the art, and so are not further described here.

The inner barrel 62 may be substantially comprised of a conductive metallic material. The instrumented section 64 can be attached at a distal end of the inner barrel 62 (e.g., by welding or threading, etc.).

In the example depicted in FIG. 2, the instrumented section 64 has an enlarged outer diameter as compared to an adjacent section of the inner barrel 62. The instrumented section 64 comprises a toroidal electromagnetic antenna 66 and longitudinally spaced apart sets of electrodes 68*a,b* to measure characteristics (e.g., voltage, current) indicative of resistivity of the core 40.

The antenna 66 is mounted circumferentially around an inner bore 70 of the assembly 62 in which the core 40 is received. Electrodes 68*a,b* are longitudinally spaced apart to detect core 40 resistivity at the spaced apart locations.

Each set of electrodes 68*a,b* preferably includes multiple electrodes circumferentially spaced apart about the bore 70. For example, there could be six or eight electrodes in each set, equally (or unequally) spaced apart encircling the bore 70. Only one electrode could be used, or any other number of electrodes may be used, in keeping with the scope of this disclosure.

In one example, the electrodes 68*a,b* may be insulated from the instrumented section 64 by insulators (not shown). Alternatively, the instrumented section 64 could be substantially made of nonconductive material. The scope of this disclosure is not limited to any particular materials used for elements of the core analysis system 34.

The antenna 66 transmits electromagnetic signals into the core 40 as it is being cut by the bit 38, thereby inducing current i in the core. The amount of current i induced in the core 40 is related to the resistivity of the core between a particular electrode 68*a,b* and the antenna 66. The current i may be detected, for example, with a toroid electromagnetic signal detector (not shown) surrounding the electrode.

An electronics module 72 is mounted in the instrumented section 64, and electronic circuitry therein is electrically coupled to the antenna 66 using known techniques. The electronics module 72 may comprise circuits, components and processors for powering, interfacing with, and controlling the antenna and receivers associated with instrumented section 64. The electronics module 72 may comprise hybrids and/or multi-chip modules to minimize space requirements and power consumption, and to improve reliability.

In the example of FIG. 2, the electronics module 72 also comprises a communications transmitter to transmit the measurement data to a separate controller 74 for retransmission of the data to the telemetry module 32. In the depicted example, an inductive coupling 76 enables communication between the electronics module 72 and the controller 74. Alternatively, the electronics module 72 may communicate with the controller 74 via radio frequency, acoustic, or any other suitable technique.

In one example, the electronics module 72 and controller 74 are each powered by batteries included therewith. Alternatively, the controller 74 may provide power to the electronics module 72 via the inductive coupling 76, electrical power could be generated downhole, etc.

The multiple measurements taken circumferentially about the core 40 by each set of electrodes 68*a,b* may disclose circumferential variations in the core resistivity. An average of the measurements may provide a bulk resistivity of the core 40 at that location.

The data from the instrumented section 64 may be used to indicate continuous movement of the core 40 into the inner barrel 62. Assuming some variations in the resistivity measurements along the core 40, and by cross correlating the measurements from the two longitudinally spaced apart sets of electrodes 68*a,b*, the velocity of the core into the inner barrel 62 can be continuously determined (velocity=displacement/time) in real time.

Since the progress of the coring bit 38 through the formation 22 can be readily measured (for example, by measuring the advancement of the drill string 16 through the rotary table 18 at the surface 14, by use of downhole logging while drilling (LWD) or measurement while drilling (MWD) sensors, etc.), this can be compared to the velocity of the core 40 into the coring bit 38. If the core 40 is not advancing into the coring bit 38, but the coring bit is advancing through the formation 22, this is an indication that the core is jammed, stuck or otherwise prevented from being received further into the inner barrel 62. If the core 40 is not advancing into the coring bit 38, and the coring bit is not advancing through the formation 22, this is an indication that the bottom hole assembly 28 is not drilling into the formation.

In another operational method, downhole depth (true vertical depth, or depth along the wellbore 20) may be tracked. As described, the measurements from the lower electrodes 68*b* may be computationally compared to the measurements made at the upper electrodes 68*a* as a function of a delay time.

When the measurements correlate, the upper electrodes 68*a* have moved a distance D between the electrodes 68*a,b* in the delay time. By tying these measurements to a previously determined benchmark position in the well, the depth of the core analysis system 34 past the benchmark can be determined. In substantially inclined boreholes, this may be a more accurate measurement than those presently used.

Figure 3:
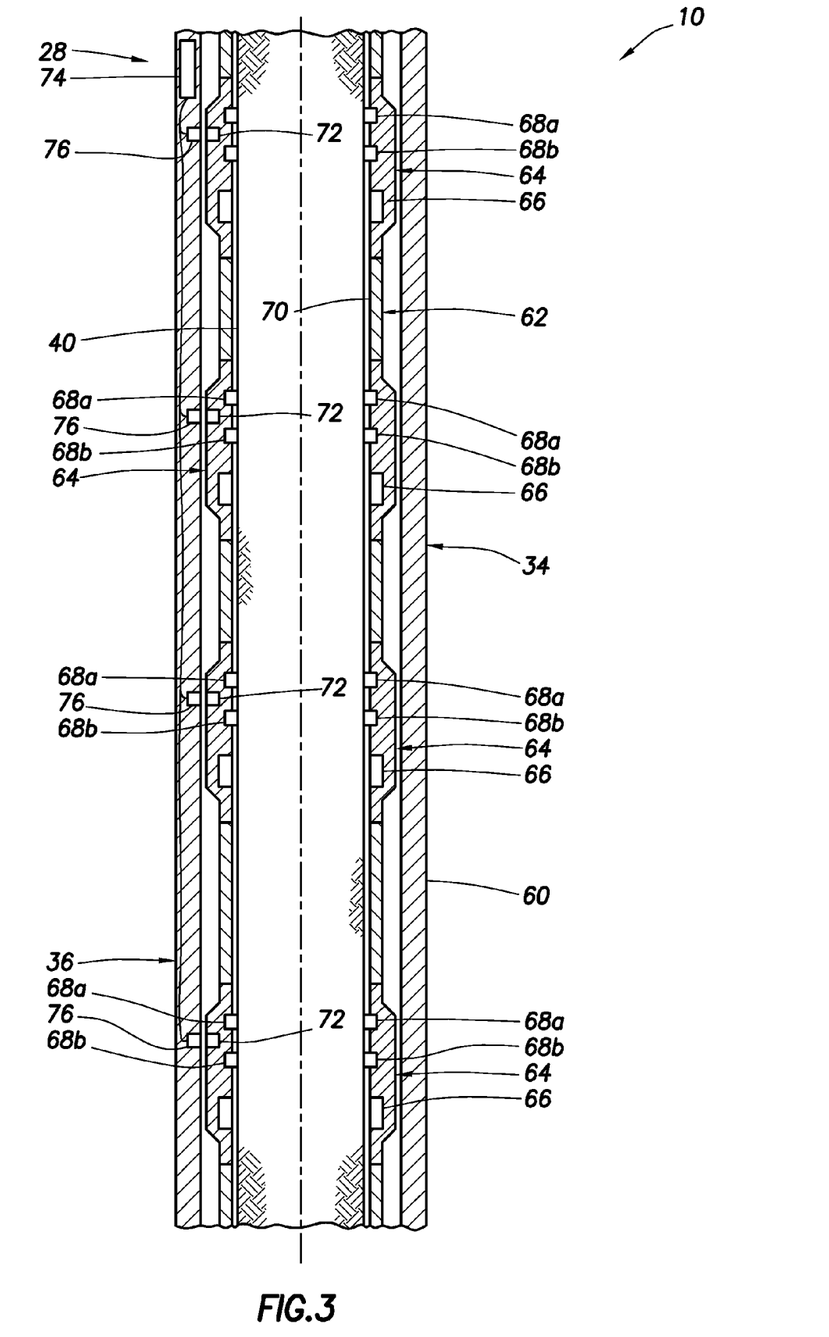
FIG. 3 is a representative cross-sectional view of another configuration of the formation core analysis system.

Referring additionally now to FIG. 3, another configuration of the core analysis system 34 is representatively illustrated. In this configuration, multiple instrumented sections 64 are interconnected in the inner barrel 62 at longitudinally spaced apart locations.

In the example depicted in FIG. 3, a single controller 74 is connected to the instrumented sections 64 via multiple inductive couplings 76. However, in other examples, a single inductive coupling 76 could be used, multiple controllers 74 could be used, etc. The scope of this disclosure is not limited to any particular number or arrangement of elements of the core analysis system 34.

Figure 4:
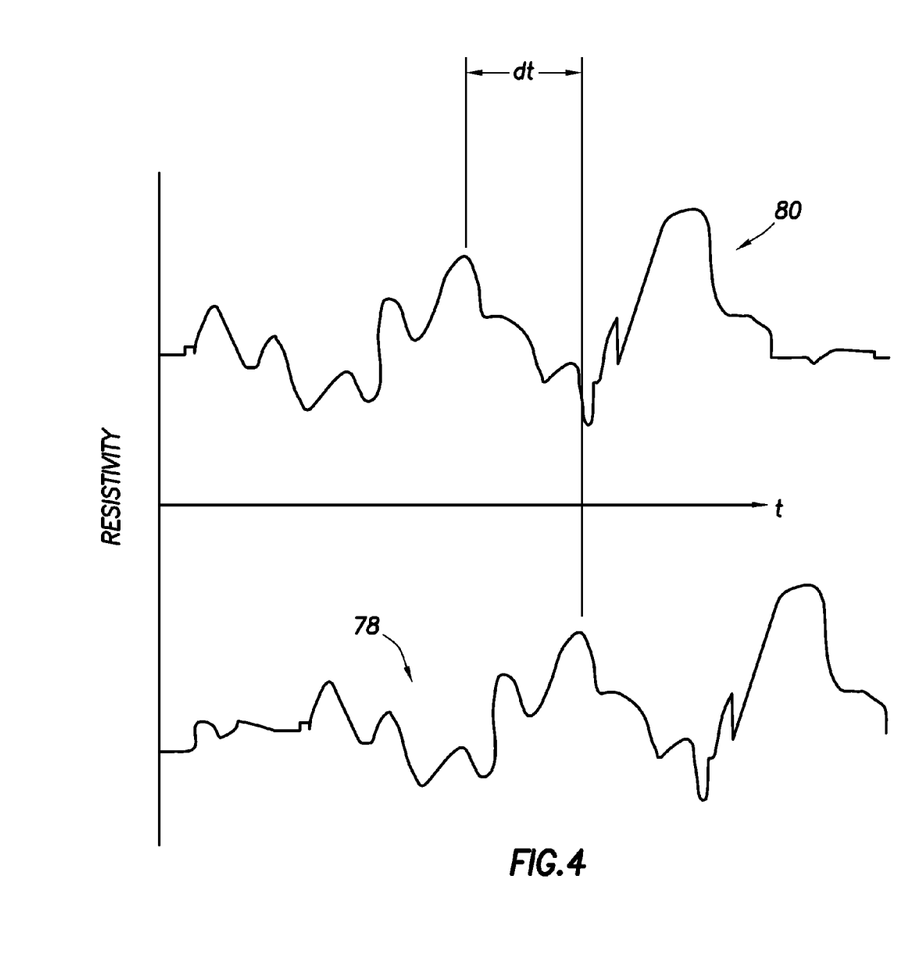
FIG. 4 is a representative graph of core resistivity over time for spaced apart electrodes in the formation core analysis system.

Referring additionally now to FIG. 4, an example of how measurements made by the electrodes 68*a,b* can be used to determine a speed of displacement of the core 40 into the inner barrel 62 while the core is being cut is representatively illustrated. In this example, graphs 78, 80 are depicted of resistivity measurements over time (resistivity along the vertical axis, and time along the horizontal axis).

The graph 78 measurements are taken by an electrode 68*a*, and the graph 80 measurements are taken by an electrode 68*b*. Note that the graphs 78, 80 are correlated by a delay time dt between the two graphs. The speed of the displacement of the core 40 into the bore 70 in this example is equal to the longitudinal distance L between the electrodes 68*a,b* divided by the delay time dt.

Although the graphs 78, 80 are for resistivity over time, it is not necessary for the measurement data transmitted from the electrodes 68*a,b* to include resistivity measurements. In some examples, the measurement data may include measurements of parameters (such as voltage, current, etc.) from which the resistivity of the core 40 can be derived.

It may now be fully appreciated that this disclosure provides significant benefits to the art of monitoring core cutting operations. In examples described above, resistivity of the core 40 can be monitored at longitudinally spaced apart locations as the core is being cut. In some examples, the toroidal antenna 66 can be used to induce a current in the core 40 as it is being received in the inner barrel 62.

A formation core analysis system 34 for use in a subterranean well is provided to the art by this disclosure. In one example, the system 34 includes an inner barrel 62, and a toroidal electromagnetic antenna 66 which transmits electromagnetic signals into a formation core 40 when the core 40 is received in the inner barrel 62.

The system 34 can include at least one electrode 68a,b which electrically contacts the core 40 when the core 40 is received in the inner barrel 62. Current i induced in the core 40 by the antenna 66 may flow between the core 40 and the electrode 68a,b.

The system 34 can include an inductive coupling 76 which transmits measurements taken via the electrode 68a,b.

The antenna 66 and the electrode 68a,b can be included in an instrumented section 64 of the inner barrel 62. A coring bit 38 which cuts the core 40 may rotate relative to the inner barrel 62. The inner barrel 62 can include multiple longitudinally spaced apart instrumented sections 64.

Also described above is a formation core analysis system 34 which can include an inner barrel 62 and multiple longitudinally spaced apart electrodes 68a,b which electrically contact a formation core 40 when the core 40 is received in the inner barrel 62. A speed of displacement of the core 40 into the inner barrel 62 can be indicated by differences between measurements taken via the electrodes 68a,b as the core 40 displaces into the inner barrel 62.

The system 34 can include a toroidal electromagnetic antenna 66 which transmits electromagnetic signals into the core 40 when the core 40 is received in the inner barrel 62.

The antenna 66 and the electrodes 68a,b may be included in an instrumented section 64 of the inner barrel 62. The electrodes 68a,b can contact the core 40 as the core 40 displaces into the inner barrel 62.

A method of measuring resistivity of a formation core 40 as the core 40 is being cut in a subterranean well is also described above. In one example, the method can include transmitting electromagnetic signals into the core 40 from a toroidal electromagnetic antenna 66 as the core 40 is being cut by a coring bit 38.

The coring bit 38 may rotate relative to the toroidal antenna 66 as the core 40 is being cut.

The toroidal antenna 66 may be included in an inner barrel 62 which receives the core 40 as it is being cut. The coring bit 38 may rotate relative to the inner barrel 62.

The method can include at least one electrode 68a,b electrically contacting the core 40 as the core 40 is being cut.

The method can include current i induced in the core 40 by the antenna 66 flowing between the core 40 and the electrode 68a,b.

The method can include an inductive coupling 76 transmitting measurements taken via the electrode 68a,b.

The antenna 66 and the electrode 68a,b can be included in an instrumented section 64 of an inner barrel 62, and the inner barrel 62 can include multiple longitudinally spaced apart instrumented sections 64.

The method may include multiple longitudinally spaced apart electrodes 68a,b electrically contacting the core 40 as the core 40 is being cut.

The method can include current i induced in the core 40 by the antenna 66 flowing between the core 40 and each of the electrodes 68a,b.

The method may include comparing the speed of displacement of the core 40 into the inner barrel 62 to a speed of displacement of the coring bit 38 through an earth formation 22. The method can also include determining whether the core 40 is jammed based on the comparing step.

A method of determining a speed of displacement of a formation core 40 into an inner barrel 62 as the core 40 is being cut can, in one example, include the steps of transmitting electromagnetic signals into the core 40 as the core 40 is being cut, thereby inducing current i in the core 40; electrically contacting the core 40 with longitudinally spaced apart electrodes 68a,b; and determining the speed of displacement of the core 40 into the inner barrel 62, based on differences between measurements taken via the electrodes 68a,b as the core 40 is being cut.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

In the above description of the representative examples, directional terms (such as "above," "below," "upper," "lower," etc.) are used for convenience in referring to the accompanying drawings. However, it should be clearly understood that the scope of this disclosure is not limited to any particular directions described herein.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. Accordingly, the foregoing detailed description is to be clearly understood as being given by way of illustration and example only, the spirit and scope of the invention being limited solely by the appended claims and their equivalents.

What is claimed is:

1. A formation core analysis system for use in a subterranean well, the system comprising:
   an inner barrel;
   a toroidal electromagnetic antenna which transmits electromagnetic signals into a formation core when the core is received in the inner barrel; and multiple longitudinally spaced apart electrodes which sequentially contact the core as the core is received in the inner barrel and thereby detect displacement of the core into the inner barrel as a result of a comparison of measurements taken by separate ones of the electrodes.

2. The system of claim 1, further comprising an inductive coupling which transmits measurements taken via the electrodes.

3. The system of claim 1, wherein the antenna and the electrodes are included in an instrumented section of the inner barrel, and wherein a coring bit which cuts the core rotates relative to the inner barrel.

4. The system of claim 3, wherein the inner barrel includes multiple longitudinally spaced apart instrumented sections.

5. The system of claim 1, wherein current induced in the core by the antenna flows between the core and each of the electrodes.

6. The system of claim 1, wherein a speed of displacement of the core into the inner barrel is indicated by differences between measurements taken via the electrodes as the core displaces into the inner barrel.

7. A formation core analysis system for use in a subterranean well, the system comprising:
an inner barrel; and
multiple longitudinally spaced apart electrodes which electrically contact a formation core when the core is received in the inner barrel, and wherein a speed of displacement of the core into the inner barrel is indicated by differences between measurements taken via different ones of the electrodes as the core displaces into the inner barrel.

8. The system of claim 7, further comprising a toroidal electromagnetic antenna which transmits electromagnetic signals into the core when the core is received in the inner barrel.

9. The system of claim 8, wherein the antenna and the electrodes are included in an instrumented section of the inner barrel, and wherein a coring bit which cuts the core rotates relative to the inner barrel.

10. The system of claim 9, wherein the inner barrel includes multiple longitudinally spaced apart instrumented sections.

11. The system of claim 8, wherein current induced in the core by the antenna flows between the core and each of the electrodes.

12. The system of claim 7, further comprising an inductive coupling which transmits measurements taken via the electrodes.

13. The system of claim 7, wherein the electrodes contact the core as the core displaces into the inner barrel.

14. A method of measuring resistivity of a formation core as the core is being cut in a subterranean well, the method comprising:
transmitting electromagnetic signals into the core from a toroidal electromagnetic antenna as the core is being cut by a coring bit;
sequentially contacting the core with multiple longitudinally spaced apart electrodes as the core is being cut; and
detecting displacement of the core into a core barrel assembly as a result of differences between measurements taken by at least a first one of the electrodes and measurements taken by at least a second one of the electrodes.

15. The method of claim 14, wherein the coring bit rotates relative to the toroidal antenna as the core is being cut.

16. The method of claim 14, wherein the toroidal antenna is included in an inner barrel which receives the core as it is being cut, and wherein the coring bit rotates relative to the inner barrel.

17. The method of claim 14, further comprising an inductive coupling transmitting measurements taken via the electrodes.

18. The method of claim 14, wherein the antenna and the electrodes are included in an instrumented section of an inner barrel of the core barrel assembly, and wherein the inner barrel includes multiple longitudinally spaced apart instrumented sections.

19. The method of claim 14, further comprising current induced in the core by the antenna flowing between the core and each of the electrodes.

20. The method of claim 14, further comprising comparing a speed of displacement of the core into the inner barrel to a speed of displacement of the coring bit through an earth formation.

21. The method of claim 20, further comprising determining whether the core is jammed based on the comparing.

22. A method of measuring resistivity of a formation core as the core is being cut in a subterranean well, the method comprising:
transmitting electromagnetic signals into the core from a toroidal electromagnetic antenna as the core is being cut by a coring bit;
contacting the core with multiple longitudinally spaced apart electrodes as the core is being cut; and
determining a speed of displacement of the core into the inner barrel, based on differences between measurements taken via different ones of the electrodes as the core is being cut.

23. A method of determining a speed of displacement of a formation core into an inner barrel as the core is being cut, the method comprising:
transmitting electromagnetic signals into the core as the core is being cut, thereby inducing current in the core;
electrically contacting the core with longitudinally spaced apart electrodes; and
determining the speed of displacement of the core into the inner barrel, based on differences between measurements taken via different ones of the electrodes as the core is being cut.

24. The method of claim 23, further comprising a toroidal electromagnetic antenna transmitting electromagnetic signals into the core as the core is being cut.

25. The method of claim 24, wherein the antenna and the electrode are included in an instrumented section of the inner barrel, and further comprising a coring bit cutting the core and rotating relative to the inner barrel.

26. The method of claim 25, wherein the inner barrel includes multiple longitudinally spaced apart instrumented sections.

27. The method of claim 24, further comprising current induced in the core by the antenna flowing between the core and each of the electrodes.

28. The method of claim 23, further comprising an inductive coupling transmitting measurements taken via the electrodes.

29. The method of claim 23, further comprising the electrodes contacting the core as the core is being cut.

30. The method of claim 23, further comprising comparing the speed of displacement of the core into the inner barrel to a speed of displacement of the coring bit through an earth formation.

31. The method of claim 30, further comprising determining whether the core is jammed based on the comparing.

* * * * *

UNITED STATES PATENT AND TRADEMARK OFFICE
CERTIFICATE OF CORRECTION

| | | |
|---|---|---|
| PATENT NO. | : 8,854,044 B2 | Page 1 of 1 |
| APPLICATION NO. | : 13/659250 | |
| DATED | : October 7, 2014 | |
| INVENTOR(S) | : Michael S. Bittar and Gary E. Weaver | |

It is certified that error appears in the above-identified patent and that said Letters Patent is hereby corrected as shown below:

Title page, Item 73, Assignee:, cancel "Haliburton" and insert in place thereof -- Halliburton --.

Signed and Sealed this
Sixth Day of January, 2015

Michelle K. Lee
*Deputy Director of the United States Patent and Trademark Office*